United States Patent
Bosch et al.

(10) Patent No.: US 6,391,563 B1
(45) Date of Patent: May 21, 2002

(54) METHOD FOR THE DETERMINATION OF ANTIGENS WITH THE AID OF THREE OR MORE MONOCLONAL ANTIBODIES

(75) Inventors: Anna M. G. Bosch; Antonius H. W. M. Schuurs, both of Oss; Wilhelmus J. H. M. Stevens, Berghem; Bauke K. van Weemen, Riethoven, all of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 08/164,581

(22) Filed: Dec. 8, 1993

Related U.S. Application Data

(63) Continuation of application No. 08/007,047, filed on Jan. 20, 1993, now abandoned, which is a continuation of application No. 07/814,232, filed on Dec. 23, 1991, now abandoned, which is a continuation of application No. 07/139,674, filed on Dec. 30, 1987, now abandoned, which is a division of application No. 06/803,083, filed on Nov. 27, 1985, now abandoned, which is a continuation of application No. 06/542,776, filed on Oct. 17, 1983, now abandoned, which is a continuation of application No. 06/281,299, filed on Jul. 7, 1981, now abandoned.

(30) Foreign Application Priority Data

Jul. 28, 1980 (NL) ............................................. 8004308

(51) Int. Cl.⁷ ................................................. G01N 33/53
(52) U.S. Cl. ..................... 435/7.1; 435/7.21; 435/7.9; 435/7.92
(58) Field of Search .............................. 435/7.1, 7.21, 435/7.92, 7.9; 436/548

(56) References Cited

U.S. PATENT DOCUMENTS

| | | | |
|---|---|---|---|
| 3,654,090 A | | 4/1972 | Schuurs et al. |
| 3,791,932 A | | 2/1974 | Schuurs et al. |
| 4,115,535 A | * | 9/1978 | Giaever |
| 4,191,739 A | * | 3/1980 | Uzgiris et al. |
| 4,196,265 A | | 4/1980 | Koprowski et al. |
| 4,361,647 A | * | 11/1982 | Remington et al. |
| 4,376,110 A | * | 3/1983 | David et al. |
| 4,486,530 A | * | 12/1984 | David et al. |

OTHER PUBLICATIONS

Ekins Nature 340: 256–258 (1989).*
Ekins in Radiopharmaceuticals II: 219–239 (1979).*
Ekins in Radiopharmaceuticals II: 241–275 (1979).*
Anon Jama 242: 2161–2163 (1979).*
Milstein Scientific American 243: 66–74 (1980).*
Staines et al. Immunology 40:287–293 (1980).*
Hunter in Weir Handbook of Exptl. Immunol. Blackwell Scientific Oxford (1979) pp. 14.1–14.40.*

(List continued on next page.)

*Primary Examiner*—Phillip Gambel
(74) *Attorney, Agent, or Firm*—William M. Blackstone; Michael G. Sullivan; Mary E. Gormley

(57) ABSTRACT

A process for the determination of the presence or concentration of a polyepitopic antigen in a specimen, comprising contacting the specimen with a first reagent comprising one or more monoclonal antibodies to form a conjugate comprising monoclonal antibodies in the first reagent and an antigen in the specimen having epitopes to which said monoclonal antibodies are immunoreactive; contacting the conjugate so formed with a second reagent comprising one or more monoclonal antibodies to form a conjugate comprising the antigen, the monoclonal antibodies from the first reagent and the monoclonal antibodies from the second reagent, wherein one of the first and second reagents comprises two different monoclonal antibodies and the antibodies in the first reagent and the antibodies in the second reagent comprises three different monoclonal antibodies reactive with different epitopes on said antigen; and detecting the conjugate comprising the antigen and the three different monoclonal antibodies.

11 Claims, 2 Drawing Sheets

OTHER PUBLICATIONS

Kwan et al. Gen Eng 2:31–46 (1980).*
Van Weemen et al. Immunochemistry 12: 667–670 (1975).*
Hagen et al. Clinica Chimica Acta 69: 193–201 (1976).*
Leuvering et al. Fresenius Z. Anal. Chem. 301:132 (1980).*
Berzofsky et al. Biochemistry 15:2113–2121 (1976).*
Fox C & EN Jan. 1, 1979 pp. 15–17.*
231 USPQ 81 (CAFC 1986).*
Zeitschr. fur Analyt. Chem 1980, 301, 132.
Proc. Natl. Acad. Sci. USA 1979, 76, pp 1438–1442.
Chemical & Engineering News vol. 57, Jan. 1, 1979.
Mol. Immunol. 1980, 17(6), pp. 791–794.
Scientific American vol. 243, 1980, pp. 56–64.
Current Topics in Microbiol. and Immunol., 81, 1978, pp xii–xvvii.
Proc. Natl. Acad. Sci. USA 1979, 76, pp. 3532–3536.

* cited by examiner

Curve

1  Gold sol covered with anti-PAG A

2  Gold sol covered with anti-PAG B

3  Gold sol covered with mixture of anti-PAG A and anti-PAG B

4  Mixture of gold sol covered with anti-PAG A and gold sol covered with anti-PAG B.

METHOD FOR THE DETERMINATION OF ANTIGENS WITH THE AID OF THREE OR MORE MONOCLONAL ANTIBODIES

This application is a continuation of U.S. Ser. No. 08/007,047 filed Jan. 20, 1993, now abandoned, which is a continuation of U.S. Ser. No. 07/814,232 filed Dec. 23, 1991, now abandoned, which is a continuation of U.S. Ser. No. 07/139,674 filed Dec. 30, 1987 now abandoned, which is a divisional application of U.S. Ser. No. 06/803,083 filed Nov. 27, 1985, now abandoned, which is a continuation of U.S. Ser. No. 06/542,776 filed Oct. 17, 1983, now abandoned, which is a continuation of U.S. Ser. No. 06/281,299 filed Jul. 7, 1981, now abandoned.

For many years it has been known that sensitive and specific methods of determination can be developed for many substances based on an immunochemical reaction, i.e., a reaction between two or more immunocomponents, such as, for example, between an antigen and antibody.

BACKGROUND OF THE INVENTION

An antigen is a substance that, if injected into an animal for which the antigen in question is foreign to the body, gives rise to the formation of an immunological defensive reaction, and an antibody is a protein molecule (an immunoglobulin) that is formed by the animal in whose blood it is present as a reaction to the penetration of the antigen, and which can enter into a specific bond with the antigen against which it is directed. Although this mechanism is in principle regarded as a defensive mechanism against harmful substances that penetrate a living organism (e.g., a virus infection), it can be used for the creation of antibodies against any arbitrary antigen. The degree of harmfulness of the antigen is of no relevance. The blood serum of such an animal, or fractions thereof containing antibodies, can be employed as a reagent for the antigen. A very large number of substances of different structure can function as antigens. Thus, in test animals antibodies are created by almost all sorts of protein molecules, against glycoproteins, against certain carbohydrates, lipids and, after the use of certain artifices, even against low-molecular substances such as steroid hormones and prosta-glandins.

This means that for all these classes of substance immunochemical methods of determination can be developed.

SUMMARY OF THE INVENTION

This invention relates to methods for determining antigens by means of an immunochemical reaction, whereby the antigen must enter into a bond with at least two antibody molecules, characterized in that two or more different sorts of monoclonal antibodies directed against the same antigen are used.

DETAILED DESCRIPTION OF THE EMBODIMENTS

Figure 1:
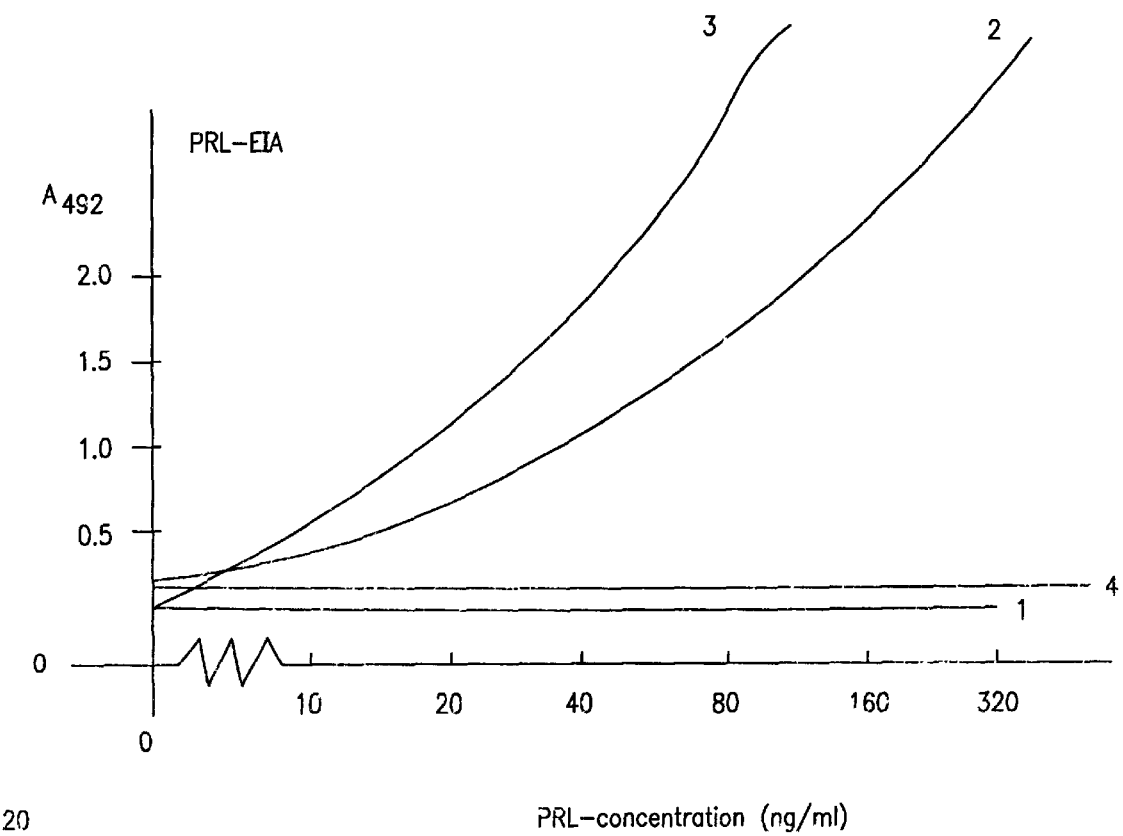
FIG. 1 illustrates dose response curves obtained by plotting measured extinctions against logarithms of the prolactin concentration using different monoclonal anti-PRL preparations.

Although, even on the basis of simple precipitation of antigens by antibodies, an immunochemical method of determination for the antigen can be developed, normally more refined methods are used to obtain the full benefit from the possibilities offered by the immunochemical reaction regarding specificity and sensitivity. In this connection, the antigen or antibody molecule is frequently provided with a label which renders the occurrence of the antigen/antibody bond visible or measurable in a simple manner.

As labels the following have, inter alia, been employed: red blood cells (haemagglutination reaction), polystyrene latex spheres (latex agglutination reaction), metal sol particles, finely suspended dyestuff particles and, frequently combined with antibody molecules that have been rendered insoluble, radioisotopes, enzymes and fluorescent substances.

The general characteristic of the type of immunochemical determinations referred to here is the fact that the antigen molecule to be determined forms a bond with at least two antibody molecules.

The classic method of creating antibodies, the injection of a test animal with antigens, normally results in an extremely heterogeneous immune response. One can assume that during this procedure in test animals, populations of antibody forming cells (lymphocytes) are stimulated, each of which produce their own sort of antibody with unique structure, affinity and specificity. Furthermore, it appears that in a test animal, in the course of time, different populations of lymphocytes can obtain the upper hand. The result of this is that it is not only very difficult to obtain from different test animals blood sera (antisera) containing antibodies of comparable quality, but also that antiserum specimens obtained from the same test animal at different points in time can be widely different from each other.

For some years now it has been possible to obtain absolutely homogeneous antibodies in practically unlimited amounts. For this purpose, use is made of a cell-free system or a modified organism, wherein genetic material coding for the desired antigen specific globulines are being expressed, for example by:

a) Cell fusion For this purpose an antibody producing cell is brought together with a continuously growing cell line, e.g., a lymphocyte cell that has become a tumor cell (myeloma cell line). Cell fusion takes place both spontaneously and under the influence of certain substances such as polyethylene glycol or lecithine, and as a fusion product a "hybridoma" forms, which both has the capacity for producing antibodies from the one cell and the continuous growth potential of the other cell involved.

b) Transformation
  1. Antibody producing cells are made to grow continuously, whether or not by transduction.
  2. Isolated and/or wholly or partly synthetically prepared nucleic acid sequences are introduced into the desired host cell.

c) Mutation By chemical or physical treatment of the antibody producing cell.

Also, combinations of the above mentioned methods can be applied, if desired.

For each separate cell line the antibodies produced are identical with those produced by the original antibody producing cell. They are, thus, perfectly homogeneous. Since these are formed from the one original antibody producing cell, we term them as monoclonal antibodies.

Monoclonal antibodies, as a result of their homogeneity and the simple manner in which they can be produced in "unlimited" quantities, are in principle particularly suitable as reagents during the immunochemical methods of determination described previously.

However, the fact has emerged that monoclonal antibodies frequently do not react in test methods in which "classical" antibodies are quite effective. Monoclonal antibodies do not form a precipitate with their corresponding antigens; particles (erythrocytes, latex spheres, metal particles) coated with monoclonal antibodies do not agglutinate in the presence of corresponding antigens; monoclonal antibodies marked with a radio isotope, an enzyme, a metal particle, and etc., do not bond to a solid phase that is coated with the monoclonal antibodies in the presence of the corresponding antigen. All this is opposed to the behaviour of "classical" antibodies.

A method has now been found for determination of an antigen by means of an immunochemical reaction, whereby the antigen must enter into a bond with at least two antibody molecules, characterised in that two or more different sorts of monoclonal antibodies are used, directed against the same antigen.

The invention similarly relates to test kits that are used for the methods of determination described for this purpose.

Cell lines producing monoclonal antibodies against the same antigen can be obtained by various methods. Normally, on cell fusion during a fusion experiment, 10–100 hybridoma lines are obtained, each of which produces an antibody of different specificity and affinity. It is advisable to characterise these cell lines in greater detail, so as to be able to select an optimum combination for an immunochemical test system.

The monoclonal antibodies can be processed in different, known, ways to provide reagents for immunochemical determination methods. Thus, for example, they can be combined by physical absorption or by covalent combination to the surface of formalin-treated erythrocytes or of polystyrene latex spheres of differing diameters, thus serving as reagent in an inverted passive haemagglutination test or latex agglutination test. Also, they can be combined by physical absorption or by inclusion with particles of a metal sol for use in immuno determination of a homogeneous or heterogeneous sol particle. Furthermore, they can be used in an analogous matter in a dyestuff particle immunodetermination, which additionally offers the facility of covalent bonding. Monoclonal antibodies can also be combined in a known chemical or physical manner with fixed substrates, such as the wall of a plastic reagent tube, plastic spheres or other objects, cellulose or sepharose particles, and etc., to serve as the solid phase in sandwich assays. Here use should at the same time be made of monoclonal antibodies that have been marked by, for example, a radioisotope, an enzyme, a fluorophore or a metal sol particle, so that the formation of an antibody/antigen bond can be observed. Numerous methods have been described in the relevant literature for all these procedures, which can be directly employed for monoclonal antibodies.

Combinations of two or more monoclonal antibodies can be obtained in various ways. For example a reagent for reversed passive haemagglutination can be prepared by mixing antibodies from two or more hybridomas and subsequently using them for the coating of erythrocytes, so that each erythrocyte carries different antibody molecules; but similarly separate batches of erythrocytes can be coated, each with one monoclonal antibody, after which these batches are mixed in an optimum proportion.

Also, for example, a "sandwich" radioimmunoassay can be obtained by coating a solid substrate with monoclonal antibody A and marking a monoclonal antibody B with 125I, but also by using a mixture of antibodies A and B for both the coating of the solid substrate and also the marking with 125I. A variety of possibilities for other test procedures is feasible in similar ways.

Some care is required in the selection of an effective combination of two or more monoclonal antibodies for use in immunochemical determination methods, as described previously.

Not every arbitrary combination of two or more antibodies will satisfy reasonable requirements regarding sensitivity and specificity, and it is even possible that such a combination will not be at all effective. Establishing the best combination depends exclusively on empiricism. In the ideal case a wide range of monoclonal antibodies is available against a certain antigen. This range is studied under all possible combinations, after which the combination is selected that supplies reliable, sensitive and specific results.

The method according to the present invention is particularly suited for the screening of samples for the presence of different antigens. For that purpose a reagent is composed consisting of particles, such as erythrocytes, latex spheres or plastic spheres, each coated with different monoclonal antibodies directed against the different antigens to be detected in the sample, and of particles, each coated with monoclonal antibodies directed against the same antigens, however the latter antibodies being of a different kind than the first-mentioned ones.

The combinations described of monoclonal antibodies, processed or not to form reagents (such as portions of surfaces coated with antibodies, or enzyme-marked antibodies) can be processed with excellent results to give immunochemical test kits: being combinations of reagents which, provided that they are used in accordance with the prescribed procedure, give test methods of specified sensitivity and reliability. Such kits can for example be made up as follows:

A pregnancy test kit consisting of a mixture of sheep erythrocytes coated with monoclonal antibodies A against human chorionic gonadotropin (HCG), and sheep erythrocytes coated with monoclonal antibodies B against HCG, freeze-dried in a glass ampoule with round bottom, which at the same time serves as the sedimentation tube for the test, or a test kit for the determination of human placenta lactogenic hormone (HPL), consisting of a microtitration plate, of which the walls of the pits are coated with monoclonal antibody A against HPL, ampoules with a freeze-dried mixture of antibodies B and C against HPL, marked with the enzyme peroxidase, and ancillary substances such as wash buffer, enzyme substrate, controls and standards.

Generally, the invention relates to a test kit consisting of the following:

1. a monoclonal antibody, or some different types of monoclonal antibodies directed against the same antigen and marked with a certain label,
2. a monoclonal antibody which differs from 1, or some different types of monoclonal antibodies directed against the same antigen, which is either insoluble or which has been made so, or which is marked or will be marked with a certain label, and
3. other suitable reagents.

The following examples are intended to illustrate but by no means restrict the scope of the invention.

EXAMPLE 1

Pregnancy Test 1.a. Preparation of Monoclonal Antibodies against HCG

Mice (strain BALB/C) were immunised with human chorionic gonadotropin (HCG) with a purity of 10.000 IU/mg. After about 6 weeks a cell suspension was prepared from the spleen, after which $8 \times 10^7$ cells thereof were fused with $2 \times 10^7$ myloma cells ($P_3 \times 63$ Ag/8/653) under conditions described in literature (Köhler and Milstein, Nature 256 (1975) 495). Hybridomas were grown in Dulbecco modified Eagle's medium with 10% fetal calf serum and investigated for anti-HCG production. Antibody producing hybridomas were recloned at least twice. Large quantities of monoclonal antibodies were obtained by re-injecting the hybridomas in the abdominal cavity of mice (strain BALB/C) and after 2–3 weeks recovering the ascites fluid.

1.b. Preparation of Sheep Erythrocytes Covered with Monoclonal anti-HCG

Sheep erythrocytes were stabilized by formalin treatment (Wide: Acta endocrinol, Suppl. 70 (1962), 20, as modified by Schuurs et al: Acta endocrinol, 59 (1968) 120) and were covered with monoclonal antibodies by incubating them for 2.5 hours with the antibodies in a concentration of 0.2 mg/ml.

1.c. Reaction of Sheep Erythrocytes Covered with Monoclonal anti-HCG with HCG and LH 0.025 ml of a solution of HCG or leutenising hormone (LH) was added to 0.5 ml of a 0.4% erythrocyte suspension in a glass tube with a round bottom. The tube contents were shaken, after which the tube was stored free from vibration for 2 hours. If no agglutination occurred, a dark brown ring became visible on the bottom of the tube (−); in the event of agglutination a smooth light brown layer formed on the bottom of the tube (+).

The results of different combinations of antibodies with HCG and the cross-reacting hormone LH are reproduced in Table 1.

Although no single erythrocyte alone led to agglutination, different combinations provided sensitive and specific pregnancy tests.

TABLE 1

| antibodies | sensitivity for HCG (IU/1) | sensitivity for LH (IU/1) |
|---|---|---|
| A;B;C;D;E; separately | >300.000 | not tested |
| A + B | 260 | >2000 |
| A + D | 200 | >2000 |
| A + E | 200 | >2000 |
| B + C | 200 | >2000 |
| C + E | 300 | >2000 |

EXAMPLE 2

Enzyme Immunoassay for Prolactin 2.a. Preparation of Monoclonal Antibodies against Prolactin (PRL)

The method employed was identical with that described in Example 1.a., whereby immunization was naturally undertaken with prolactin.

2.b. Preparation of Coupling Products of Monoclonal anti-PRL with Peroxidase

The Ig fraction of monoclonal anti-PRL obtained from mouse ascites liquid was coupled with the enzyme horseradish peroxidase (HRP) with the aid of sodium periodate, as described by Nakane and Wilson (in: Immunofluorescence and Related Staining Techniques; Knapp, Holubar, Wick (Editors); Elsevier, Amsterdam, 1978).

2.c. Preparation of Micropits Covered with Monoclonal anti-PRL

The pits of polystyrene microtitration plates were filled with 0.1 ml of a solution of the Ig fraction of mouse ascites fluid (see 2.a.) with a concentration of 5 µg/ml and incubated overnight at room temperature. After this the pits were washed with phosphate buffer which 37° C. Then the pits were extracted and washed four times with phosphate buffer with Tween-20.

Then the pits were filled with 0.1 ml of a solution of a monoclonal anti-PRL-HRP coupling product (see 2.b.), covered and incubated for 2 hours at 37° C. After renewed extraction and washing, the pits were filled with a solution of O-phenylene-diamine.2HCl and ureumperoxide (substrate for the enzyme HRP). After 30 minutes incubation of the enzyme reaction was stopped by adding 0.1 ml of 2 mol/l sulphuric acid and extinction was measured at 492 nm.

Finally dose-response curves were constructed by plotting the measured extinctions against the logarithms of the PRL concentration in the solutions that were first placed in the pits. A number of these curves obtained with different monoclonal anti-PRL preparations are reproduced in FIG. 1.

EXAMPLE 3

Sol Particle Immunoassay for PAG 3.a. Preparation of Monoclonal Antibodies against PAG The method used was identical with that described in example 1.a., whereby natural immunization was undertaken with pregnancy associated $\alpha_2$ glycoprotein (PAG).

3.b. Preparation of a Gold Sol covered with Monoclonal anti-PAG

Gold sols with an average particle size of 60 nm were prepared in accordance with the method described by Frens (Nature Phys. Sci. 241 (1973), 20) and subsequently coated with the Ig fraction of mouse ascites fluid (see 3.a.) as described by Leuvering, Thal, van der Waart and Schuurs (J. Immunoassay 1 (1980) 77).

3.c. Determination of PAG

Of the gold sol covered with anti-PAG prepared in section 3.b., 0.9 ml was mixed with 0.1 ml of solutions having different contents of PAG. The mixtures were incubated for 1 hour at room temperature, after which extinction was measured at 540 nm.

Figure 2:
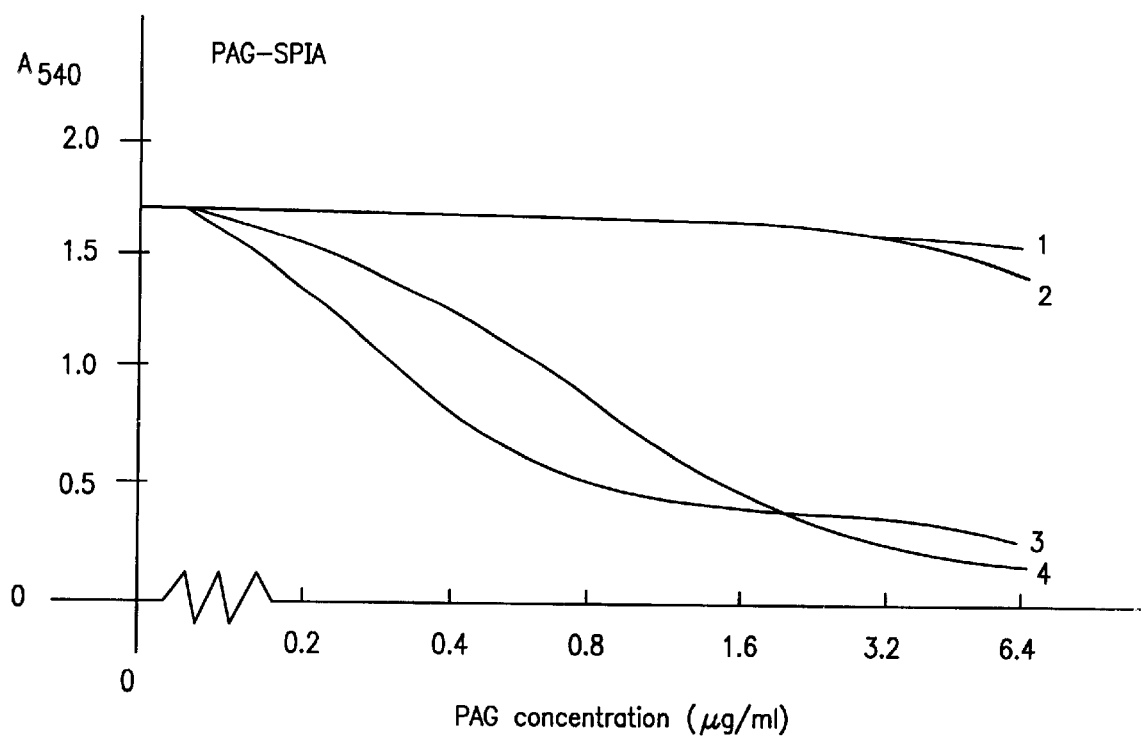
FIG. 2 illustrates dose response curves obtained by plotting measured extinctions against the logarithm of pregnancy associated $\alpha_2$-glycoprotein (PAG) using a variety of anti-PAG antibody compositions.

Dose-response curves were obtained by plotting the measured extinctions against the logarithm of the PAG concentration. A number of these curves are shown in FIG. 2.

EXAMPLE 4

Latex Agglutination Test for PAP 4.a. Preparation of Monoclonal Antibodies against Human Plasmine-antiplasmine Complex (PAP) in Accordance with the Methods described in Example 1.a.

Only the monoclonal antibodies were used in the experiments described in the following which could admittedly react with the PAP complex, but not with the separate constituent parts (plasmine, antiplasmine).

4.b. Preparation of Latex Covered with Monoclonal anti-PAP

Polystyrene latex with a particle diameter of 0.8µ was covered with the Ig fraction of mouse ascites fluids which contained monoclonal anti-PAP (see Example 4.a.) in accordance with the method of Singer and Plotz (Amer.J.Med. 21 (1956) 888).

4.c. Determination of PAP

On a glass test plate size 4×4 cm 1 drop of anti-PAP latex suspension (see Example 4.b.) and 1 drop of normal human plasma (NHP) or normal human plasma treated with urokinase (UNHP) was mixed and then spread over as large a surface as possible, after which the liquid was kept for 3 minutes in steady uniform movement. Visible granulation of the latex suspension was noted as a positive result, while if the suspension remained smooth it was regarded as negative. It was possible to establish a PAP titer in a plasma specimen by testing a series of dilutions, whereby the highest dilution which still gave a positive result was regarded as the titer. It should be understood that NHP contains little or no PAP, and that UNHP contains a maximum quantity of PAP. Thus a wide difference between the NHP titer and UNHP titer is the desired result.

The results obtained with a number of monoclonal antibodies are shown in Table 2. This illustrates the results obtained with mixtures of latex suspensions, each coated with only one monoclonal anti-PAP but also the results of latex suspensions coated with mixtures of 2 or 3 monoclonal anti-PAP's.

TABLE 2

PAP-latex agglutination

A. Mixture of latex suspension coated with a monoclonal anti-PAP.

|  | Latex A | Latex B | Latex C |
| --- | --- | --- | --- |
| Latex A | NHP < 16<br>U-NHP < 16 | NHP < 16<br>U-NHP 128 | NHP < 16<br>U-NHP 128 |
| Latex B |  | NHP < 1/16<br>U-NHP < 1/16 | NHP < 16<br>U-NHP 256 |
| Latex C |  |  | NHP < 16<br>U-NHP < 16 |

A mixture of equal parts of latex A, B and C gave a NHP titer of < 16, whilst the UNHP titer was 512;

B. Latex coated with mixtures of monoclonal anti-PAP latex coated with a mixture of anti-PAP's, A, B and C supplied a UNHP titer of 512–1024, whilst the NHP titer was <16.

Latex coated with a mixture of anti-PAP's A, B and C supplied a UNHP titer of 512–1024, whilst the NHP titer was <16.

What is claimed is:

1. A process for the determination of the presence or concentration of a polyepitopic antigen in a specimen, comprising:

contacting the specimen with a first reagent comprising one or more monoclonal antibodies to form a conjugate comprising monoclonal antibodies in the first reagent and an antigen in the specimen having epitopes to which said monoclonal antibodies are immunoreactive; contacting the conjugate so formed with a second reagent comprising one or more monoclonal antibodies to form a conjugate comprising the antigen, the monoclonal antibodies from the first reagent and the monoclonal antibodies from the second reagent, wherein one of the first and second reagents comprises two different monoclonal antibodies and the antibodies in the first reagent and the antibodies in the second reagent consist of three different monoclonal antibodies reactive with different epitopes on said antigen; and detecting the conjugate comprising the antigen and the three different monoclonal antibodies.

2. The process of claim 1, wherein at least one of the three different monoclonal antibodies contains a detectable label.

3. The process of claim 1, wherein at least one of the three different monoclonal antibodies is insoluble.

4. The process of claim 2, wherein at least one of the three different monoclonal antibodies is insoluble.

5. The process of claim 3, wherein the insoluble monoclonal antibody is bound to a solid substrate.

6. The process of claim 1, wherein the specimen is contacted with the first reagent and the second reagent simultaneously.

7. The process of claim 1, wherein the specimen is separated from the conjugate comprising the antigen and antibodies from the first reagent before contacting said conjugate with the second reagent.

8. The process of claim 7, wherein the conjugate is washed before contacting with the second reagent.

9. The process of claim 5, wherein the solid substrate is selected from the group consisting of a reagent tube, a microtitre plate, cellulose, and sepharose particles.

10. The process of claim 2, wherein the label is selected from the group consisting of a radioisotope, an enzyme, a fluorophore, a dye sol particle, a metal sol particle and a metal compound sol particle.

11. A process for the determination of the presence or concentration of a polyepitopic antigen in a specimen, comprising:

contacting the specimen with a first reagent comprising one or more monoclonal antibodies to form a conjugate comprising monoclonal antibodies in the first reagent and an antigen in the specimen having epitopes to which said monoclonal antibodies are immunoreactive, said antigen being selected from the group consisting of HCG, LH PRL, PAG and PAP antigens; contacting the conjugate so formed with a second reagent comprising one or more monoclonal antibodies to form a conjugate comprising the antigen, the monoclonal antibodies from the first reagent and the monoclonal antibodies from the second reagent, wherein one of the first and second reagents comprises two different monoclonal antibodies and the antibodies in the first reagent and the antibodies in the second reagent consist of three different monoclonal antibodies reactive with different epitopes on said antigen; and detecting the conjugate comprising the antigen and the three different monoclonal antibodies.

* * * * *